United States Patent
Vogt et al.

(10) Patent No.: US 7,030,093 B2
(45) Date of Patent: Apr. 18, 2006

(54) ANTIBIOTIC COATING FOR POROUS BODIES AND METHOD FOR ITS PRODUCTION AS WELL AS ITS USE

(75) Inventors: Sebastian Vogt, Jena (DE); Matthias Schnabelrauch, Jena (DE); Klaus-Dieter Kühn, Marburg (DE)

(73) Assignee: HERAEUS Kulzer GmbH & Co. KG, Hanau (DE)

( * ) Notice: Subject to any disclaimer, the term of this patent is extended or adjusted under 35 U.S.C. 154(b) by 0 days.

(21) Appl. No.: 10/600,548

(22) Filed: Jun. 20, 2003

(65) Prior Publication Data

US 2004/0048786 A1    Mar. 11, 2004

(30) Foreign Application Priority Data

Jun. 21, 2002    (DE) ............................... 102 27 935

(51) Int. Cl.
*A61K 31/70*    (2006.01)
*C07H 15/00*    (2006.01)

(52) U.S. Cl. ........................ 514/25; 514/27; 514/28; 514/29; 623/1.11; 424/422; 536/16.8

(58) Field of Classification Search ............ 514/29, 514/28, 25, 27; 623/11.11, 1.11; 424/422; 536/16.8
See application file for complete search history.

(56) References Cited

U.S. PATENT DOCUMENTS

| | | | | |
|---|---|---|---|---|
| 3,091,572 | A | 5/1963 | Luedemann et al. | 167/65 |
| 4,291,013 | A | 9/1981 | Wahlig et al. | 424/16 |
| 4,617,293 | A | 10/1986 | Wahlig et al. | 514/41 |
| 4,713,076 | A * | 12/1987 | Draenert | 623/23.6 |
| 4,749,585 | A * | 6/1988 | Greco et al. | 428/422 |
| 5,679,646 | A | 10/1997 | Cimbollek et al. | 514/43 |
| 2003/0096097 | A1 | 5/2003 | Vogt et al. | 428/304.4 |

FOREIGN PATENT DOCUMENTS

| | | |
|---|---|---|
| CA | 1 237 672 | 6/1988 |
| DE | 2 301 633 | 11/1973 |
| DE | 24 46 640 A1 | 12/1975 |
| DE | 28 07 132 A1 | 8/1979 |
| DE | 32 48 328 | 6/1984 |
| DE | 32 48 328 A1 | 6/1984 |
| DE | 33 48 328 A1 | 6/1984 |
| DE | 36 13 213 A1 | 10/1987 |
| DE | 43 14 871 A1 | 11/1994 |
| DE | 199 10 188 A1 | 5/2000 |
| DE | 101 14 245 A1 | 10/2002 |
| DE | 101 14 364 A1 | 10/2002 |
| EP | 0 633 032 A1 | 1/1995 |
| EP | 0 667 161 B1 | 8/1995 |
| EP | 0 985 413 A1 | 3/2000 |
| EP | 1 287 818 A1 | 3/2003 |

OTHER PUBLICATIONS

European Search Report, dated Sep. 26, 2003, for EP 03 01 1967.

* cited by examiner

*Primary Examiner*—Samuel Barts
*Assistant Examiner*—Michael C. Henry
(74) *Attorney, Agent, or Firm*—Norris McLaughlin & Marcus PA

(57) ABSTRACT

The invention describes an antibiotic coating for porous bodies and its use. Into the porous system of non-metallic porous bodies and of metallic porous bodies, a coating made of at least one antibiotic salt that is hardly soluble in water or in an aqueous environment from the group of the netilmicin laurate, the netilmicin myristate, the netilmicin dodecyl sulfate, the sisomicin laurate, the sisomicin myristate, the sisomicin dodecyl sulfate, the gentamicin laurate, the gentamicin myristate, the clindamycin laurate, the amikacin laurate, the amikacin myristate, the amikacin dodecyl sulfate, the kanamycin laurate, the kanamycin myristate, the kanamycin dodecyl sulfate, the tobramycin laurate, the tobramycin myristate, the tobramycin dodecyl sulfate, the ciprofloxacin myristate, the vancomycin dodecyl sulfate, the vancomycin laurate, the vancomycin myristate, the vancomycin teicoplanin and the clindamycin teicoplanin is introduced. The antibiotically coated, porous bodies are used as implants.

15 Claims, No Drawings

ANTIBIOTIC COATING FOR POROUS BODIES AND METHOD FOR ITS PRODUCTION AS WELL AS ITS USE

The present invention relates to an antibiotic coating for (interconnecting) porous bodies and a method for its production as well as its use. These antibiotically equipped porous bodies shall be used as implants in human and veterinary medicine for the treatment of bone defects and possibly for the treatment of soft tissue defects. It is desired that a continuous release of the antibiotic from the antibiotic coating located on the inner surface of the porous systems over a period of several days takes place in order to effectively prevent or fight a bacterial infection in the area of the bone defect and/or the soft tissue defect that needs to be treated. In particular such bacterial pathogens that have developed resistance towards conventionally used antibiotics shall be treated.

Bone defects occur relatively frequently in human and veterinary medicine and are caused in particular through bone fistulas, partial fractures and tumors. In the case of open partial fractures, frequently additionally infections of the bone tissue are observed. The treatment of bone defects can occur through a filling process with suitable implants. Over the last few years in particular porous implants, which due to their chemical composition and their porous structure have an osteoconductive effect and favor a joining with the surrounding bone tissue, have gained interest. The treatment of bone defects becomes problematic whenever additionally microbial infections of the bone tissue exist. Infections of the bone tissue can be counteracted through the systemic or local application of suitable antibiotics after prior surgical reconstruction. The systemic application of antibiotics is problematic due to the in part quite considerable toxicity of the antibiotics. The local application directly in or on the infected tissue, after appropriate surgical reconstruction, however offers the advantage that high local antibiotics concentrations can be achieved while avoiding damaging antibiotics concentrations in the remaining organism. These high local antibiotics concentrations at the location of the bacterial infection allow the microorganisms to be killed almost completely so that the bacterial infections can be treated very efficiently. It is particularly beneficial if at the location of the bacterial infections an effective antibiotic concentration is maintained over the course of several days to weeks so as to allow the antibiotic to penetrate into the infected tissue as deeply as possible and thus destroy even germs that are difficult to access. Soft tissue defects with bacterial infections can also be found frequently in human and veterinary medicine. Local antibiotics application is therefore also of interest for the treatment of these types of infections.

Until now hardly soluble salts of the aminoglycoside antibiotics and the lincosamide antibiotics met with relatively little interest in the production of controlled-release drugs and of antibiotically effective implants. Among the aminoglycoside antibiotics just a few slightly soluble salts are known. E.g. for gentamicin the presentation of slightly soluble salts based on higher fatty acids, arylalkyl carboxylic acids, alkyl sulfates and alkyl sulfonates has been described (G. M. Luedemann, M. J. Weinstein: Gentamycin and method of production. Jul. 16, 1962, U.S. Pat. No. 3,091,572). Examples of this are gentamicin salts of lauric acid, stearic acid, palmitic acid, oleic acid, phenyl butyric acid, naphthalene-1-carboxylic acid. The synthesis of dodecyl sulfates of gentamicin in an aqueous or aqueous-methanolic solution is described by Jurado Soler et al. (A. Jurado Soler, J. A. Ortiz Hernandez, C. Ciuro Bertran: Neue Gentamicinderivate (new gentamicin derivatives), Verfahren zur Herstellung derselben und diese enthaltende antibiotisch wirksame Zusammensetzung (method for production of same and antibiotically effective composition containing it). Sep. 30, 1974, DE 24 46 640). These salts however often proved to be unfavorable because they represent wax-like, hydrophobic substances, which impair galenical usage. Furthermore fatty acid salts and aliphatic sulfates of gentamicin and of etamycin were synthesized from the free base or its salts in water at 50–80° C. (H. Voege, P. Stadler, H. J. Zeiler, S. Samaan, K. G. Metzger: Schwerlösliche Salze von Aminoglykosiden sowie diese enthaltende Formulierungen verzögerter Wirkstoff-Freigabe (hardly soluble salts of aminoglycosides as well as formulations containing them with delayed active substance release). Dec. 28, 1982, DE 32 48 328). These antibiotics fatty acid salts are said to be suited as injection drugs. Hardly soluble aminoglycoside flavonoid phosphates represent a more recent development (H. Wahlig, E. Dingeldein, R. Kirchlechner, D. Orth, W. Rogalski: Flavonoid phosphate salts of aminoglycoside antibiotics, Oct. 13, 1986, U.S. Pat. No. 4,617,293). It describes the salts of phosphoric acid mono-esters of derivatives of hydroxy flavanes, hydroxy flavenes, hydroxy flavanones, hydroxy flavones and hydroxy flavylium. Particularly preferred are the derivatives of the flavanones and flavones. These hardly soluble salts are supposed to be used as controlled-release drugs. For example these salts are introduced into collagen fleece (H. Wahlig, E. Dingeldein, D. Braun: Medicinally useful, shaped mass of collagen resorbable in the body. Sep. 22, 1981, U.S. Pat. No. 4,291,013). Furthermore also artificial heart valves were impregnated with these hardly soluble gentamicin salts, Gentamicin Crobefat (M. Cimbollek, B. Nies, R. Wenz, J. Kreuter: Antibiotic-impregnated heart valve sewing rings for treatment and prophylaxis of bacterial endocarditis. Antimicrob. Agents Chemother. 40(6) (1996)1432–1437).

The production of simple controlled-released antibiotic(s) drugs in the porous systems of porous bodies through the impregnation of porous bodies with aqueous antibiotics solutions is general knowledge (R. Reiner, W. Kißing, H. Döring, K. Köster, H. Heide: Implantierbares Pharmaka-Depot (implantable controlled-release pharmaceutics). Feb. 20, 1978, DE 28 07 132). A retarding active ingredient release of the water soluble active ingredient can be accomplished only through adsorption and/or through diffusion processes, which depends on the material that is used, the pore volume and porosity. Apart from that it is also possible to dissolve slightly water soluble antibiotics salts in suitable organic solvents and impregnate the molded bodies with these solutions. This creates deposits of active ingredients in the molded bodies, which have a retarding active ingredient release effect. One example is the method for dissolving a hardly water soluble gentamicin salt and its usage for coating purposes described by Cimbollek and Nies (M.

Cimbollek, B. Nies: Solvent for a sparingly soluble gentamicin salt. May 4, 1994, U.S. Pat. No. 5,679,646). This gentamicin salt on the basis of 3-p-methoxy bezylidene-6-hydroxy-4'-methoxy flavanone-6-phosphate however must be synthesized before the coating process. Kurtz describes an interesting variation in which hardly water soluble antibiotics salts are formed in situ on a substrate that is not explained in detail through the consecutive impregnation with a solution of an alkaline gentamicin salt or a polymycin salt and an acid penicillin or cephalosporin salt under precipitation (L. D. Kurtz: Wasserunlösliche biocide Antibiotikasalze (water-insoluble biocide antibiotics salts). Nov. 13, 1973, DE 23 01 633). The penicillin or cephalosporin radicals form the anionic component of the salts, and the cationic aminoglycoside radicals form the cationic component.

This interesting coating concept was not addressed any more later on and was also not checked for its suitability for other hardly water soluble salts of the aminoglycoside antibiotics, the lincosamide antibiotics and the glycopeptide antibiotics. So far no similar impregnation methods for the production of controlled-release antibiotics drugs in porous bodies while utilizing anionic radicals from the groups of the fatty acid salts are known.

The layer-forming properties of hardly water soluble antibiotics salts on the basis of fatty acid salts and alkyl sulfates also did not receive any attention so far.

In summary it should be noted that so far no methods are known where antibiotic coatings are applied to the surface of interconnecting porous systems, which consist of hardly water soluble salts of netilmicin, sisomicin, kanamycin, amikacin, vancomycin and clindamicin and which are synthesized directly in the porous systems that are supposed to be coated starting with water soluble salts of netilmicin, sisomicin, kanamycin, amikacin, vancomycin as well as clindamicin and water soluble fatty acid salts and/or alkyl sulfates.

The present invention is based on the task of developing an antibiotic coating for porous bodies, which continuously releases antibiotics in an aqueous environment in a delayed fashion over a period of several days to a few weeks.

The task is resolved with the features of the present invention as broadly and preferably described hereinbelow.

The invention is based upon the surprising finding that the laureates and dodecyl sulfates of netilmicin and sisomicin are hardly water soluble and due to their adhesive consistency adhere to non-metallic and metallic surfaces without requiring polymeric layer-forming agents. In these salts, netilmicin and sisomicin represent the cationic component of the antibiotics salts, and the laurate radicals and the dodecyl sulfate radicals represent the anionic component. These salts dissolve slowly in an aqueous environment while releasing netilmicin and/or sisomicin. In the following, the term netilmicin laurates shall be understood as the mono-, di-, tri- and tetra-laurates of netilmicin. The term sisomicin laurates shall be interpreted as the mono-, di-, tri- and tetra-laurates of sisomicin. The myristates of these antibiotics shall be interpreted accordingly. The laurates of netilmicin and sisomicin beneficially dissolve in methanol and ethanol. The coating adheres without polymeric binding agents to the inner surface of the porous systems of porous bodies and dissolves completely in an aqueous environment while continuously releasing the antibiotics.

The invention is furthermore based on the surprising finding that clindamycin forms hardly soluble salts both with lauric acid and with teicoplanin, which can create coatings in porous systems. These salts dissolve slowly while releasing clindamycin, and in the case of clindamycin-teicoplanin while releasing both antibiotics.

The invention is additionally based on the finding that vancomycin reacts with teicoplanin to form a hardly water soluble complex, which is also suited for producing coatings. The laurate, myristate and dodecyl sulfate of vancomycin surprisingly are also sparingly water soluble. These salts are also suited for producing coatings and release vancomycin in an aqueous environment with a retarding effect.

The invention is furthermore based on the surprising finding that water soluble amikacin salts and kanamycin salts form hardly water soluble salts with water soluble salts of the lauric acid, myristic acid and dodecyl sulphuric acid. The term amikacin laurate shall be interpreted as the mono-, di-, tri- and tetra-laurates of amikacin. The term kanamycin laurate is used in a similar fashion. The terms amikacin myristate and kanamycin myristate comprise the mono-, di-, tri- and tetra-myristates of these antibiotics. Amikacin laurate and kanamycin laurate dissolve partially in mixtures of dioxane and water and also in mixtures of tetrahydrofurane and water. Amikacin laurate, amikacin myristate, amikacin dodecyl sulfate, kanamycin laurate, kanamycin myristate and kanamycin dodecyl sulfate release the underlying antibiotics in an aqueous environment in a delayed fashion.

The gentamicin salts of lauric acid and myristic acid surprisingly have a wax-like consistency and adhere very well to various non-metallic and metallic surfaces. These salts as well release gentamicin with delay in an aqueous environment. The term gentamicin laurate shall be understood as the mono-, di-, tri-, tetra- and penta-laurates of gentamicin. The term gentamicin myristate is used accordingly.

It was found surprisingly that the laurate, myristate and dodecyl sulfate of vancomycin are hardly water soluble and can form layers on surfaces. These salts release vancomycin with delay in an aqueous environment.

The laurate, myristate and dodecyl sulfate of tobramycin are likewise hardly water soluble and can be used for layer-formation purposes.

Pursuant to the invention a coating of at least one antibiotic salt that is hardly soluble in water or in an aqueous environment from the group of the netilmicin laurate, the netilmicin myristate, the netilmicin dodecyl sulfate, the sisomicin laurate, the sisomicin myristate, the sisomicin dodecyl sulfate, the gentamicin laurate, the gentamicin myristate, the clindamycin laurate, the amikacin laurate, the amikacin myristate, the amikacin dodecyl sulfate, the kanamycin laurate, the kanamycin myristate, the kanamycin dodecyl sulfate, the tobramycin laurate, the tobramycin myristate, the tobramycin dodecyl sulfate, the vancomycin laurate, the vancomycin myristate, the vancomycin dodecyl sulfate and the clindamycin teicoplanin is introduced into the porous system of non-metallic porous bodies and/or of metallic porous bodies.

Pursuant to the invention, first an aqueous solution, which contains at least one representative of an easily water soluble salt of netilmicin, sisomicin, clindamycin, amikacin, kanamycin, tobramycin and vancomycin, is introduced into the porous system of the porous bodies and then after a drying phase a second aqueous solution of an easily water soluble salt of lauric acid, myristic acid and/or dodecyl sulphuric acid is introduced and hereby a hardly water soluble antibiotic coating is formed in the porous system of the porous body.

According to the invention the sequence of the coating steps can be reversed.

It is also according to the invention that a methanolic solution or an ethanolic solution of at least one representative of the netilmicin laurate, netilmicin dodecyl sulfate, the sisomicin laurate, the sisomicin dodecyl sulfate, the gentamicin laurate, the vancomycin laurate, the vancomycin dodecyl sulfate, the clindamycin laurate and the clindamycin teicoplanin is introduced into the porous system of the porous body and that through subsequent vaporization or evaporation of the methanol or the ethanol a hardly water soluble antibiotic coating is formed.

Pursuant to the invention amikacin laurate, kanamycin laurate, amikacin dodecyl sulfate and kanamycin dodecyl sulfate are partially dissolved and/or suspended in a dioxane-water and/or tetrahydrofurane-water mixture, and these solutions and/or suspensions are introduced into the porous system of the porous bodies, and a hardly water soluble antibiotic coating is formed through vaporization or evaporation of the dioxane-water mixtures or the tetrahydrofurane-water mixtures.

It is useful if the antibiotic coating is applied to porous bodies existing in the form of porous powders, porous granules, porous molded bodies and/or porous layers on compact bodies.

The coating for porous bodies, which preferably take on the form of porous powders and/or porous granules, beneficially is formed through the addition of at least one antibiotics salt that is hardly soluble in water or in an aqueous environment from the group of the netilmicin laurate, the netilmicin myristate, the netilmicin dodecyl sulfate, the sisomicin laurate, the sisomicin myristate, the sisomicin dodecyl sulfate, the gentamicin laurate, the gentamicin myristate, the clindamycin laurate, the amikacin laurate, the amikacin dodecyl sulfate, the kanamycin laurate, the kanamycin dodecyl sulfate, the tobramycin laurate, the tobramycin myristate, the tobramycin dodecyl sulfate, the vancomycin laurate, the vancomycin myristate, the vancomycin dodecyl sulfate and the clindamycin teicoplanin, particularly through a grinding process, possibly while adding methanol, ethanol, dioxane, tetrahydrofurane and/or water or mixtures thereof.

It is beneficial that the coating for porous bodies, which preferably take on the shape of porous powders and/or porous granules, occurs through the addition, particularly a grinding process of these powders and/or granules with a mixture of at least one water soluble salt of netilmicin, sisomicin, clindamycin, amikacin, kanamycin, vancomycin and at least one water soluble salt of lauric acid and/or myristic acid and/or dodecyl sulphuric acid in the presence of water or aqueous solutions.

It is also useful if the coating possibly additionally contains easily water soluble salts of gentamicin, netilmicin, sisomicin, amikacin, kanamycin, clindamycin, tobramycin, vancomycin, ciprofloxacin and/or moxifloxacin.

The antibiotic coating is beneficially applied to resorbable porous bodies, to partially resorbable porous bodies and/or non-resorbable, bio-compatible, porous bodies.

It is also the object of the invention that the antibiotically coated bodies in the form of coated porous granules and/or coated porous powders are pressed into molded bodies, which are then used as implants.

Pursuant to the invention, the antibiotically coated porous granules and/or antibiotically coated porous powders are used as binding agents for the production of molded bodies by pressing powder mixtures.

Also pursuant to the invention, the antibiotically coated bodies are used as temporary and/or permanent implants.

It is essential for the invention that hardly water soluble salts from the group of the group of the netilmicin laurate, the netilmicin myristate, the netilmicin dodecyl sulfate, the sisomicin laurate, the sisomicin myristate, the sisomicin dodecyl sulfate, the amikacin laurate, the amikacin myristate, the amikacin dodecyl sulfate, the kanamycin laurate, the kanamycin myristate, the kanamycin dodecyl sulfate, the vancomycin dodecyl sulfate, the vancomycin laurate, the vancomycin myristate, the ciprofloxacin myristate and the clindamycin laurate are used as the controlled-release antibiotic/antibiotics preparation for implants.

The invention shall be explained in the following based on the examples 1–3, without limiting the invention.

Cuboid, resorbable phosphate glasses with the dimensions 20×20×10 mm were used as bodies with interconnecting porous systems in the examples 1–3. These bodies had an overall porosity of 65 percent by volume. 50 percent thereof were macro-pores (250–300 µm pore diameter) and 15 percent were micro-pores (pore diameter <100 µm).

EXAMPLE 1

80 mg gentamicin sulfate (AK628) were dissolved in 1.92 g bidist. water (solution 1). Separately, 75 mg sodium laurate were dissolved in 1 g of a 50% water-ethanol mixture (solution 2). First the previously prepared solution 1 was dripped into the pores of the cuboid phosphate glasses. The sample bodies absorbed the solution 1. Afterwards the water in the pores was removed through a drying process with anhydrous calcium chloride. Then the prepared solution 2 was dripped into the pores of the dried phosphate glasses. Drying of the sample bodies also took place with anhydrous calcium chloride until mass constancy.

EXAMPLE 2

80 mg clindamycin hydrochloride were dissolved in 1.92 g bidist. water (solution 1). Separately, 20 mg sodium laurate were dissolved in 1 g of water (solution 2). First the previously prepared solution 1 was dripped into the pores of the cuboid phosphate glasses. The sample bodies absorbed the solution 1. Afterwards the water in the pores was removed through a drying process with anhydrous calcium chloride. Then the prepared solution 2 was dripped into the pores of the dried phosphate glasses. Drying of the sample bodies also took place with anhydrous calcium chloride until mass constancy.

EXAMPLE 3

80 mg kanamycin sulfate were dissolved in 1.92 g bidist. water (solution 1). Separately, 93 mg sodium laurate were dissolved in 1 g of a 50% water-ethanol mixture (solution 2). First the previously prepared solution 1 was dripped into the pores of the cuboid phosphate glasses. The sample bodies absorbed the solution 1. Afterwards the water in the pores was removed through a drying process with anhydrous calcium chloride. Then the prepared solution 2 was dripped into the pores of the dried phosphate glasses. Drying of the sample bodies also took place with anhydrous calcium chloride until mass constancy.

The masses of the added antibiotics and of the sodium laurate were determined gravimetrically.

TABLE 1

|  | Mass of Added Antibiotic [mg] | Mass of Added Sodium Laurate [mg] |
|---|---|---|
| Example 1 | 59.1 | 72.0 |
| Example 2 | 58.6 | 18.3 |
| Example 3 | 61.8 | 91.0 |

The molded bodies coated in the examples 1–3 were each introduced into 10 ml Sörensen buffer with pH 7.4 and stored in it at 37° C. over a period of 12 days. Sampling took place on a daily basis. After each sampling, the release medium was replaced completely with a new medium. The release of the antibiotics was determined with an agar diffusion test while employing *bacillus subtilis* ATCC 6633 as test germ, and the inhibiting areola diameter was scanned and subsequently evaluated with the help of special software. The results are depicted in Table 2. In the case of example 1, the respectively released quantity of gentamicin was quantitatively determined with the help of gentamicin standards.

TABLE 2

| | Release of Antibiotics | | | | | |
|---|---|---|---|---|---|---|
| | Example 1 | | Example 2 | | Example 3 | |
| Time [d] | Dilution | Inhibiting Areola Diameter [mm] | Dilution | Inhibiting Areola Diameter [mm] | Dilution | Inhibiting Areola Diameter [mm] |
| 1 | 1:250 | 20.05 | 1:100 | 20.30 | 1:100 | 21.00 |
| 2 | 1:100 | 17.10 | 1:20 | 18.65 | 1:40 | 21.50 |
| 3 | 1:40 | 19.43 | 1:10 | 18.73 | 1:10 | 22.00 |
| 6 | 1:5 | 20.20 | Undiluted | 15.13 | 1:5 | 22.20 |
| 9 | Undiluted | 22.50 | Undiluted | 0.00 | 1:3 | 19.95 |
| 12 | Undiluted | 23.35 | undiluted | 0.00 | Undiluted | 23.00 |

TABLE 3

| Time [d] | 1 | 2 | 3 | 6 | 9 | 12 |
|---|---|---|---|---|---|---|
| Release of Gentamicin (as gentamicin base) [mg] | 16.28 | 2.97 | 1.65 | 0.19 | 0.09 | 0.11 |

What is claimed is:

1. Antibiotic coated porous bodies consisting essentially of a coating made of at least one antibiotic salt that is hardly soluble in water or in an aqueous environment from the group consisting of the netilmicin laurate, the netilmicin dodecyl sulfate, the netilmicin myristate, the sisomicin laurate, the sisomicin myristate, the sisomicin dodecyl sulfate, the gentamicin laurate, the gentamicin myristate, the clindamycin laurate, the amikacin laurate, the amikacin myristate, the amikacin dodecyl sulfate, the kanamycin laurate, the kanamycin myristate, the kanamycin dodecyl sulfate, the vancomycin laurate, the vancomycin dodecyl sulfate, the vancomycin myristate, the vancomycin teicoplanin, the tobramycin laurate, the tobramycin myristate, the tobramycin dodecyl sulfate, the ciprofloxacin laurate, the ciprofloxacin myristate and the clindamycin teicoplanin, said coating being introduced onto an inner surface into a porous system of non-metallic porous bodies and/or of metallic porous bodies.

2. Method for producing antibiotic coated porous bodies pursuant to claim 1, comprising introducing first an aqueous solution, containing at least one representative of an easily water soluble salt of at least one of netilmicin, sisomicin, clindamycin, amikacin, kanamycin, tobramycin, vancomycin, and ciprofloxacin, onto an inner surface of porous bodies, and that after a drying phase, introducing a second aqueous solution of an easily water soluble salt of lauric acid, myristic acid and/or dodecyl sulphuric acid and thereby developing a hardly water soluble antibiotic coating on an inner surface in the porous system of the porous body.

3. Method pursuant to claim 2, wherein the sequence of the introducing steps is reversed.

4. Method for producing antibiotic coated porous bodies pursuant to claim 1, comprising introducing a methanolic solution or an ethanolic solution of at least one representative from the group consisting of the netilmicin laurate, the netilmicin myristate, the netilmicin dodecyl sulfate, the sisomicin laurate, the sisomicin myristate, the sisomicin dodecyl sulfate, the gentamicin laurate, the gentamicin myristate, the clindamycin laurate, the tobramycin laurate, the tobramycin myristate, the tobramycin dodecyl sulfate, the ciprofloxacin myristate, the vancomycin teicoplanin and the clindamycin teicoplanin onto an inner surface into the porous system of porous bodies and vaporizing or evaporating methanol or ethanol to form a hardly water soluble antibiotic coating.

5. Method for producing antibiotic coated porous bodies pursuant to claim 1, comprising partially dissolving and/or suspending in a dioxane-water and/or in a tetrahydrofurane-water mixture amikacin laurate, kanamycin laurate, amikacin dodecyl sulfate and/or kanamycin dodecyl sulfate to form solutions and/or suspensions and introducing these solutions and/or suspensions onto an inner surface into the porous system of the porous bodies and vaporizing or evaporating the dioxane and water mixtures or the tetrahydrofurane and water mixtures to form an antibiotic coating that is hardly soluble in water.

6. Antibiotic coated porous bodies pursuant to claim 1, wherein the antibiotic coating is applied to porous bodies existing in the form of porous powders, porous granules, porous molded bodies and/or porous layers on compact bodies.

7. Antibiotic coated porous bodies pursuant to claim 1, wherein the coating for porous bodies, which optionally exists in the form of porous powders and/or porous granules, is produced through a grinding process by the addition of at least one antibiotic salt that is hardly soluble in water or in an aqueous environment from the group consisting of the netilmicin laurate, the netilmicin myristate, the netilmicin dodecyl sulfate, the sisomicin laurate, the sisomicin myristate, the sisomicin dodecyl sulfate, the gentamicin laurate, the gentamicin myristate, the clindamycin laurate, the amikacin laurate, the amikacin myristate, the amikacin dodecyl sulfate, the kanamycin laurate, the kanamycin myristate, the kanamycin dodecyl sulfate, the ciprofloxacin myristate, the tobramycin laurate, the tobramycin myristate, the tobramycin dodecyl sulfate, the vancomycin laurate, the vancomycin myristate, the vancomycin dodecyl sulfate, the vancomycin teicoplanin and the clindamycin teicoplanin, in the presence of methanol, ethanol, dioxane, tetrahydrofurane and/or water or mixtures thereof.

8. Antibiotic coated porous bodies pursuant to claim 1, wherein the coating for porous bodies, which optionally exists in the form of porous powders and/or porous granules, is produced through a grinding process by the addition of a mixture of at least one water soluble salt of netilmicin, sisomicin, clindamycin, amikacin, kanamycin, tobramycin, vancomycin and/or ciprofloxacin and at least one water soluble salt of lauric acid, myristic acid and/or dodecyl sulphuric acid in the presence of water or aqueous solutions.

9. Antibiotic coated porous bodies pursuant to claim 1, wherein the coating additionally contains easily water soluble salts of gentamicin, netilmicin, sisomicin, amikacin, kanamycin, clindamycin, tobramycin, vancomycin, ciprofloxacin and/or moxifloxacin.

10. Antibiotic coated porous bodies pursuant to claim 1, wherein the antibiotic coating is applied to resorbable porous bodies, to partially resorbable porous bodies and/or to non-resorbable, bio-compatible porous bodies.

11. Implants comprising antibiotic coated porous bodies pursuant to claim 1, which have been pressed into molded bodies with a shape of coated porous granules and/or coated porous powders.

12. Binding agents for the production of molded bodies through a pressing operation of powder mixtures, comprising antibiotic coated porous bodies pursuant to claim 1, which have been designed as antibiotically coated porous granules and/or antibiotically coated porous powders.

13. Temporary or permanent implants comprising antibiotic coated porous bodies pursuant to claim 1.

14. Antibiotic coated porous bodies pursuant to claim 1, with hardly water soluble salts from the group of the netilmicin laurate, the netilmicin myristate, the netilmicin dodecyl sulfate, the sisomicin laurate, the sisomicin myristate, the sisomicin dodecyl sulfate, the amikacin laurate, the amikacin myristate, the amikacin dodecyl sulfate, the kanamycin laurate, the kanamycin myristate, the kanamycin dodecyl sulfate, the tobramycin laurate, the tobramycin myristate, the tobramycin dodecyl sulfate, the vancomycin laurate, the vancomycin myristate, the vancomycin dodecyl sulfate, the ciprofloxacin laurate, the ciprofloxacin myristate and/or the clindamycin laurate.

15. Implants comprising antibiotic coated porous bodies pursuant to claim 14.

* * * * *